US00PP20138P2

(12) United States Plant Patent
Kanaya

(10) Patent No.: US PP20,138 P2
(45) Date of Patent: Jun. 30, 2009

(54) ***CALIBRACHOA* PLANT NAMED 'SUNBELRIRENI'**

(50) Latin Name: ***Calibrachoa* sp.**
Varietal Denomination: Sunbelrireni

(75) Inventor: Takeshi Kanaya, Tokyo (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/157,314

(22) Filed: Jun. 9, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Annette H Para
(74) *Attorney, Agent, or Firm*—C. A. Whealy

(57) ABSTRACT

A new and distinct cultivar of *Calibrachoa* plant named 'Sunbelrireni', characterized by its upright to outwardly spreading plant habit; vigorous growth habit; freely branching and flowering plant habit; long flowering period; large dark red-colored flowers; and good garden performance.

1 Drawing Sheet

Botanical designation: *Calibrachoa sp.*
Cultivar denomination: 'Sunbelrireni'.

BACKGROUND OF THE INVENTION

The present invention relates to a new and distinct cultivar of *Calibrachoa,* botanically known as *Calibrachoa sp.* and hereinafter referred to by the name 'Sunbelrireni'.

The new *Calibrachoa* is a product of a planned breeding program conducted by the Inventor in Higashiomi, Shiga, Japan. The objective of the breeding program is to develop new uniform *Calibrachoa* cultivars with attractive and unique flower coloration.

The new *Calibrachoa* originated from a cross-pollination conducted by the Inventor in Higashiomi, Shiga, Japan in April, 2004 of a proprietary selection of *Calibrachoa sp.* identified as code number H4, not patented, as the female, or seed, parent with a proprietary selection of *Calibrachoa sp.* identified as code number B12, not patented, as the male, or pollen, parent. The new *Calibrachoa* was discovered and selected by the Inventor as a flowering plant from within the progeny of the stated cross-pollination in a controlled greenhouse environment in Higashiomi, Shiga, Japan.

Asexual reproduction of the new *Calibrachoa* by vegetative cuttings in a controlled greenhouse environment in Higashiomi, Shiga, Japan since September, 2006, has shown that the unique features of this new *Calibrachoa* are stable and reproduced true to type in successive generations.

SUMMARY OF THE INVENTION

The new *Calibrachoa* has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunbelrireni'. These characteristics in combination distinguish 'Sunbelrireni' as a new and distinct cultivar of *Calibrachoa:*

1. Upright to outwardly spreading plant habit.
2. Vigorous growth habit.

3. Freely branching and flowering plant habit.
4. Long flowering period.
5. Large dark red-colored flowers.
6. Good garden performance.

Plants of the new *Calibrachoa* can be compared to plants of the female parent selection. Plants of the new *Calibrachoa* differ from plants of the female parent selection in the following characteristics:

1. Plants of the new *Calibrachoa* have larger flowers than plants of the female parent selection.
2. Plants of the new *Calibrachoa* and the female parent selection differ in flower color as plants of the female parent selection have red purple-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are taller than plants of the male parent selection.
2. Plants of the new *Calibrachoa* are broader than plants of the male parent selection.

Plants of the new *Calibrachoa* can also be compared to plants of 'Sunbelre', disclosed in U.S. Plant Pat. No. 14,756. In side-by-side comparisons conducted in Higashiomi, Shiga, Japan, plants of the new *Calibrachoa* and 'Sunbelre' differed in the following characteristics:

1. Plants of the new *Calibrachoa* were shorter than plants of 'Sunbelre'.
2. Plants of the new *Calibrachoa* had larger flowers than plants of 'Sunbelre'.
3. Plants of the new *Calibrachoa* and 'Sunbelre' differed slightly in flower color.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa*.

The photograph at the top of the sheet comprises a side perspective view of a typical flowering plant of 'Sunbelrireni' grown in a container.

The photograph at the bottom of the sheet comprises a close-up view of typical flowers of 'Sunbelrireni'.

DETAILED BOTANICAL DESCRIPTION

The aforementioned photographs and following observations, measurements and values describe plants grown in Higashiomi, Shiga, Japan, under commercial practice during the late spring and early summer in a polyethylene-covered greenhouse. During the production of the plants, day temperatures averaged 23° C. and night temperatures averaged 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Calibrachoa sp.* 'Sunbelrireni'.

Parentage:

*Female, or seed, parent.*—Proprietary selection of *Calibrachoa sp.* identified as code number H4, not patented.

*Male, or pollen, parent.*—Proprietary selection of *Calibrachoa sp.* identified as code number B12, not patented.

Propagation:

*Type.*—By vegetative cuttings.

*Time to initiate roots.*—About one week at 20° C. to 25° C.

*Time to produce a rooted young plant.*—About three weeks at 20° C. to 25° C.

*Root description.*—Fine, fibrous, fleshy; light brown in color.

*Rooting habit.*—Freely branching.

Plant description:

*Plant and growth habit.*—Upright to outwardly spreading plant habit. Freely branching with about five primary lateral branches developing per plant; pinching enhances lateral branch development. Vigorous growth habit.

*Plant height.*—About 19.9 cm.

*Plant diameter.*—About 44.1 cm.

Lateral branch description:

*Length.*—About 22.5 cm.

*Diameter.*—About 1.9 mm.

*Internode length.*—About 1 cm.

*Strength.*—Strong.

*Aspect.*—Upright to outward.

*Texture.*—Pubescent.

*Color.*—Close to 144B overlain with close to 200A.

Foliage description:

*Arrangement.*—Alternate, simple.

*Length.*—About 3.6 cm.

*Width.*—About 1 cm.

*Shape.*—Lanceolate.

*Apex.*—Broadly acute.

*Base.*—Cuneate.

*Margin.*—Entire.

*Texture, upper and lower surfaces.*—Pubescent.

*Venation pattern.*—Pinnate; reticulate.

*Color.*—Developing and fully expanded foliage, upper surface: Close to 137A; venation, close to 145A. Developing and fully expanded foliage, lower surface: Close to 137B; venation, close to 145A.

*Petiole.*—Length: About 2.2 mm. Diameter: About 0.8 mm. Texture, upper and lower surfaces: Sparsely pubescent. Color, upper and lower surfaces: Close to 145A overlain with close to 200A.

Flower description:

*Flower arrangement and habit.*—Single salverform flowers arising from upper leaf axils. Freely flowering habit with usually about 16 flowers per plant at one time. Flowers face upright or outwardly.

*Fragrance.*—Not detected.

*Natural flowering season.*—Plants of the new *Calibrachoa* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant. Flowers not persistent.

*Flower diameter.*—About 3.9 cm.

*Flower length (depth).*—About 2.9 cm.

*Throat diameter.*—About 8.5 mm.

*Tube length.*—About 1.9 cm.

*Tube diameter.*—About 2.2 mm.

*Flower bud.*—Shape: Cylindrical. Length: About 2.6 cm. Diameter: About 7.8 mm. Color: Close to N186D.

*Corolla.*—Arrangement: Five petals fused at the base and opening into a flared trumpet. Petal length from throat: About 1.7 cm. Petal width: About 1.8 cm. Petal shape: Spatulate. Petal apex: Obtuse. Petal margin: Entire. Petal texture, upper and lower surfaces: Smooth, glabrous; velvety. Throat texture: Smooth, glabrous. Tube texture: Pubescent. Color: Petal, when opening, upper surface: Close to 53A; venation, close to N187A. Petal, when opening, lower surface: Close to 59C; venation, close to 59C. Petal, fully opened, upper surface: Close to 53A; towards the throat, close to 187A; venation, close to N186B; color becoming closer to 59C with development. Petal, fully opened, lower surface: Close to 59C; venation, close to 59C. Throat: Close to 12A; venation, close to 187A. Tube: Close to 8B; venation, close to N187A.

*Calyx.*—Arrangement: One star-shaped calyx tube with five sepals fused at the base per flower. Sepal length: About 8.9 mm to 15.5 mm. Sepal width: About 3.4 mm. Sepal shape: Lanceolate. Sepal apex: Obtuse. Sepal margin: Entire. Sepal texture, upper and lower surfaces: Pubescent. Color, immature and mature, upper surface: Close to 138A. Color, immature and mature, lower surface: Close to 138B.

*Peduncles.*—Length: About 1.7 cm. Diameter: About 0.9 mm. Angle: Upright to outward. Strength: Strong. Texture: Smooth, glabrous. Color: Close to 144B overlain with close to 200A.

*Reproductive organs.*—Stamens: Quantity/arrangement: Five per flower. Stamen length: About 12.2 mm to 14.8 mm. Anther shape: Ellipsoidal. Anther size: About 1.4 mm by 1.7 mm. Anther color: Close to 14C. Pollen amount: Moderate. Pollen color: Close to 13C. Pistils: Quantity: One per flower. Pistil length: About 1.1 cm. Style color: Close to 144D. Stigma shape: Transversely ellipsoidal. Stigma color: Close to 144C. Ovary color: Close to 144D. Seed/fruit: Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Sunbelrireni' as illustrated and described.

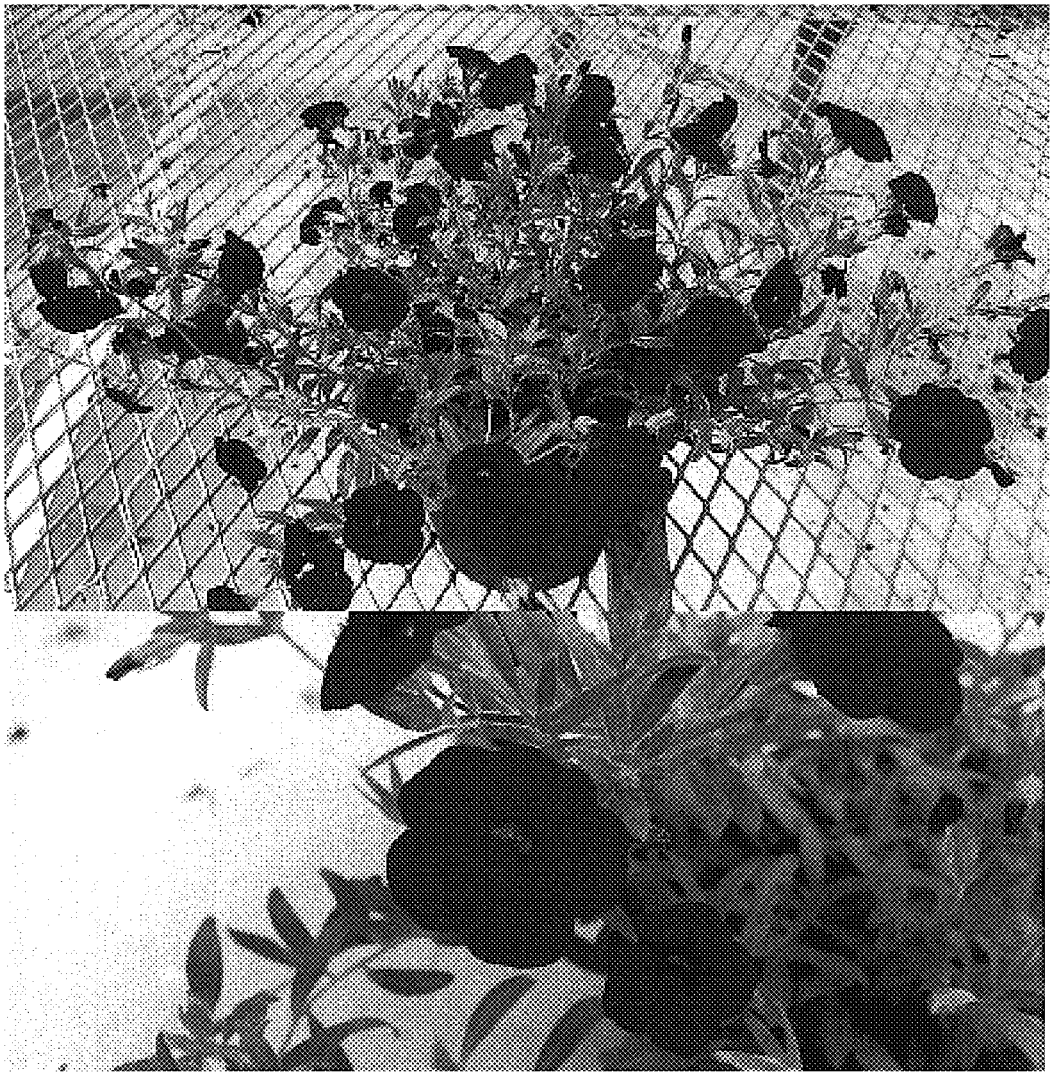

* * * * *